US006926965B2

(12) United States Patent
Qiu et al.

(10) Patent No.: US 6,926,965 B2
(45) Date of Patent: Aug. 9, 2005

(54) LBL-COATED MEDICAL DEVICE AND METHOD FOR MAKING THE SAME

(75) Inventors: Yongxing Qiu, Duluth, GA (US); Lynn Cook Winterton, Alpharetta, GA (US); John Martin Lally, Lilburn, GA (US)

(73) Assignee: Novartis AG, Basel (CH)

(*) Notice: Subject to any disclaimer, the term of this patent is extended or adjusted under 35 U.S.C. 154(b) by 0 days.

(21) Appl. No.: 10/654,566

(22) Filed: Sep. 3, 2003

(65) Prior Publication Data

US 2004/0067365 A1 Apr. 8, 2004

Related U.S. Application Data

(60) Provisional application No. 60/409,950, filed on Sep. 11, 2002.

(51) Int. Cl.$^7$ .................. B32B 25/20; B32B 27/08; B32B 27/30; G02C 7/04
(52) U.S. Cl. .................. 428/411.1; 428/447; 428/500; 523/107; 523/108; 351/160 R; 351/160 H
(58) Field of Search .................. 523/16, 107, 108; 351/160 R, 160 H; 428/411.1, 447, 500

(56) References Cited

U.S. PATENT DOCUMENTS

| | | | |
|---|---|---|---|
| 4,168,112 A | 9/1979 | Ellis et al. .................. 351/160 |
| 4,321,261 A | 3/1982 | Ellis et al. .................. 424/180 |
| 4,941,997 A | 7/1990 | Decher et al. .............. 252/586 |
| 4,973,429 A | 11/1990 | Decher et al. .............. 252/587 |
| 5,068,318 A | 11/1991 | Decher et al. .............. 534/573 |
| 5,208,111 A | 5/1993 | Decher et al. .............. 428/420 |
| 5,509,899 A | * 4/1996 | Fan et al. .............. 604/103.14 |
| 5,518,767 A | 5/1996 | Rubner et al. .............. 427/259 |
| 5,529,727 A | 6/1996 | LaBombard et al. ....... 264/1.36 |
| 5,536,573 A | 7/1996 | Rubner et al. .............. 427/378 |
| 5,700,559 A | 12/1997 | Sheu et al. .............. 428/319.7 |
| 6,011,082 A | 1/2000 | Wang et al. .................. 523/107 |
| 6,451,871 B1 | 9/2002 | Winterton et al. .......... 523/106 |
| 6,531,432 B2 | 3/2003 | Molock et al. ............. 510/112 |
| 6,699,435 B2 | 3/2004 | Salpekar et al. .............. 422/40 |
| 2001/0045676 A1 | 11/2001 | Winterton et al. ........... 264/2.5 |
| 2001/0048975 A1 | 12/2001 | Winterton et al. ........ 427/412.1 |
| 2002/0006493 A1 | 1/2002 | Chabrecek et al. ......... 428/64.1 |
| 2002/0086160 A1 | 7/2002 | Qiu et al. .................. 428/413 |
| 2002/0182316 A1 | 12/2002 | Gilliard et al. .............. 427/162 |
| 2003/0008154 A1 | 1/2003 | Aguado et al. ............. 428/447 |
| 2003/0012872 A1 | 1/2003 | Qiu et al. .................. 427/162 |
| 2003/0039742 A1 | 2/2003 | Qiu et al. .................. 427/2.1 |
| 2003/0052424 A1 | 3/2003 | Turner et al. .............. 264/1.32 |
| 2003/0117579 A1 | 6/2003 | Morris et al. .............. 351/200 |
| 2003/0125498 A1 | 7/2003 | McCabe et al. .............. 528/25 |
| 2003/0134132 A1 | 7/2003 | Winterton et al. .......... 428/451 |
| 2003/0162862 A1 | 8/2003 | McCabe et al. ............. 523/106 |

FOREIGN PATENT DOCUMENTS

| | | |
|---|---|---|
| EP | 0 032 443 | 5/1985 |
| EP | 0 138 385 | 4/1990 |
| EP | 0 995 762 | 4/2000 |
| GB | 2 102 070 | 1/1983 |
| JP | 07256844 | 10/1995 |
| WO | WO 95/00618 | 1/1995 |
| WO | WO 95/02251 | 1/1995 |
| WO | WO 95/20407 | 8/1995 |
| WO | WO 96/18498 | 6/1996 |
| WO | WO 96/31792 | 10/1996 |
| WO | WO 96/37241 | 11/1996 |
| WO | WO 99/35520 | 7/1999 |
| WO | WO 01/57118 | 8/2001 |
| WO | WO 01/92924 | 12/2001 |
| WO | WO 02/16974 | 2/2002 |
| WO | WO 02/097481 | 12/2002 |
| WO | WO 03/066714 | 8/2003 |

OTHER PUBLICATIONS

International Search Report, Dec. 2003.

European Search Report, Mar. 2003.

Decher, Lehr, Lowack, Lvov & Schmitt, "New Nanocomposite Films for Biosensors: layer by Layer adsorbed films of polyelectrolytes, proteins or DNA",1994, pp677–684.

Sukhorukov, Mohwald, Decher and Lvov, "Assembly of Polyelectrolyte Multilayer films by consecutively alternating adsorption of Polynucleotides and Polycations", 1996, pp. 220–223.

Uchida, Kunitake, and Kajiyama, "Blood Compatibility—Surface Characteristic Relationship of a Langmuir–Blodgett Film COmposed of an Anionic Amphiphile–Polycation COmplex", 1994, pp. 199–211.

Onitsuka, Fou, Ferreira, Hsieh, and Rubner, "Enhancement of Light Emitting Diodes Based on Self–Assembled Heterostructures of Poly(p–PHenylene Vinylene)", 1996, pp. 4067–4071.

Yoo, Lee and Rybner, "Investigations of New Self–Assembled MultiLayer Thin Films Based on Alternately Adsorbed Layers of Polyelectrolytes and Functional Dye Molecules", 1996, pp. 395–400.

Yoo, Wu, Lee and Rubner, "New Electro–Active Self–Assembled MultiLayer Thin Films Based on Alternately Adsorbed Layers of Polyelectrolytes and Functional Dye Molecules", 1997, pp. 1425–1426.

(Continued)

*Primary Examiner*—Ramsey Zacharia
(74) *Attorney, Agent, or Firm*—Jian S. Zhou; Robert J. Gorman

(57) ABSTRACT

The present invention provides a medical device, preferably an ophthalmic device, more preferably a contact lens, which comprises a core material and a biocompatible LbL coating non-covalently attached to said core material. The biocompatible LbL coating comprises at least one charge/non-charge bilayer, wherein said charge/non-charge bilayer is composed of, in no particular order, one layer of a charged polymeric material and one layer of a non-charged polymeric material which is capable of being non-covalently bond to the charged polymeric material.

13 Claims, No Drawings

OTHER PUBLICATIONS

Yoo & rubner, "Layer–By–Layer Modification of Surfaces Through The USe of Self Assembled Monolayers of Polyions", 1995, pp. 2568–174.

Ferreira and Rubner, "Molecular Level Processing of Conjugated Polymers. Layer by Layer Manipulation of Conjugated Polyions", 1995, pp. 7107–7114.

Fou and Rubner, "Molecular Level Processing of Conjugated Polymers. Layer by Layer Manipulation of In–Situ Polymerized p–Type Doped Conducting Polymers", 1995, pp. 7115–7120.

Cheung, Stockton & Rubner, "Molecular Level Processing of Conjugated Polymers. Layer by Layer Manipulation of Polyanilene via Electrostatic Interactions", 1995, pp. 2712–2716.

Cheung, Fou, Ferreira and Rubner, "Molecular Self Assembly of Conducting Polymers: A New Layer by Layer Thin Film Deposition Process", pp. 757–758.

Vargo, Clavert, Wynne Avlyanov, MacDiarmid, and Rubner, "Patterned Polymer multilayer Fabrication by Controlled Adhesion of Polyelectrolytes to Plasma modified Fluoropolymer Surfaces", 1996, pp. 169–174.

* cited by examiner

LBL-COATED MEDICAL DEVICE AND METHOD FOR MAKING THE SAME

This application claims the benefit under USC §119)e) of U.S. provisional application Ser. No. 60/409,950 filed Sep. 11, 2002, incorporated by reference in its entirety.

The present invention generally relates to a medical device having a biocompatible LbL coating thereon. In particular, the present invention relates to an ophthalmic device having a biocompatible LbL coating that comprises at least one bilayer of a charged polymeric material and a non-charged polymeric material which is non-covalently bonded to the charged polymeric material. In addition, this invention provides a method for making a medical device having a biocompatible LbL coating of the invention.

BACKGROUND OF THE INVENTION

Many devices used in biomedical applications require that the bulk of the devices have one property and the surfaces of the device have a different property. For example, contact lenses may require relatively high oxygen permeability through the bulk of the lens to maintain good corneal health. However, materials that exhibit exceptionally high oxygen permeability (e.g. polysiloxanes) are typically hydrophobic and, will up take lipid or protein from the ocular environment and may adhere to the eye if not treated or surface-modified. Thus, a contact lens will generally have a core or bulk material that is highly oxygen permeable and hydrophobic, and a surface that has been treated or coated to increase hydrophilic properties. This hydrophilic surface allows the lens to move relatively freely on the eye without absorbing excessive amounts of tear lipid and protein.

In order to modify the hydrophilic nature of a relatively hydrophobic contact lens material, a coating may be applied onto the surface of a contact lens using a number of technologies, including a plasma treatment process (e.g., PCT Publication Nos. WO 96/31793, WO 99/57581, WO 94/06485), a Langmuir-Blodgett deposition process (e.g., U.S. Pat. Nos. 4,941,997; 4,973,429; and 5,068,318), a controlled spin casting process, a chemisorption process, a vapor deposition or a layer-by-layer polymer adsorption process that is preceded by a charge inducing process. These techniques are not cost-effective and are difficult to be implemented in an automated production process.

Another coating technique is a layer-by-layer ("LbL") polyelectrolyte absorption process. For example, Yoo, et al. reported a process which involves alternatively dipping hydrophilic glass substrates in a polyelectrolyte solution (e.g., polycations such as polyallylamine or polyethyleneimine) and then in an oppositely charged solution to form electrically conducting thin films and light-emitting diodides (LEDs) (Yoo, et al., "Investigation of New Self-Assembled Multilayer Thin Films Based on Alternately Adsorbed Layers of Polyelectrolytes and Functional Dye Molecules", Mat. Res. Soc. Symp. Proc. 413: 395–400 (1996)).

A series of three articles described similar LbL polyelectrolyte absorption processes (Ferreira & Rubner, Macromolecules, 28: 7107–7114 (1995); Fou & Rubner, Macromolecules, 28: 7115–7120 (1995); and Cheung et al., Macromolecules, 30:2712–2716 (1997)). These processes involve treating glass substrates that have hydrophilic, hydrophobic, negatively, or positively charged surfaces. The glass surfaces are treated for extended periods in hot acid baths and peroxide/ammonia baths to produce a hydrophilic surface. Hydrophobic surfaces are produced by gas-phase treatment in the presence of 1,1,1,3,3,3-hexamethyldisilazine for 36 hours. Charged surfaces are prepared by covalently anchoring charges onto the surface of the hydrophilic slides. For example, positively charged surfaces are made by further treating the hydrophilic surfaces in methanol, methanol/toluene, and pure toluene rinses, followed by immersion in (N-2 aminoethyl-3-aminopropyl) trimethyloxysilane solution for 12 to 15 hours. This procedure produces glass slides with amine functionalities, which are positively charged at a low pH.

U.S. Pat. Nos. 5,518,767 and 5,536,573 to Rubner et al. describe methods of producing bilayers of p-type doped electrically conductive polycationic polymers and polyanions or water-soluble, non-ionic polymers on glass substrates. These patents describe extensive chemical pretreatments of glass substrates that are similar to those described in the aforementioned articles.

U.S. Pat. No. 5,208,111 to Decher et al. describes a method for applying one or more layers to a support modified by the applications of ions and ionizable compounds of the same charges over the entire area. The one or more layers are made of organic materials which in each layer contain ions of the same charge, the ions of the first layer having the opposite charge of the modified support and in the case of several layers each further layer having again the opposite charge of the previous layer.

U.S. Pat. No. 5,700,559 to Sheu et al. discloses a method for making a hydrophilic article having a substrate, an ionic polymeric layer bonded directly onto the substrate, and a disordered polyelectrolyte coating tonically bonded to the ionic polymeric layer. The ionic polymeric layer is obtained by a plasma treatment, an electron beam treatment, a corona discharge, an X-ray treatment, or an acid/base chemical modification of the substrate.

Although each of these surface modification techniques are effective for producing an article with a surface that is different from the remainder of the article, the modification processes requires complex and time-consuming pretreatment of the substrate surface. To overcome this problem, various layer-by-layer (LbL) polyelectrolyte deposition techniques have been developed by the assignee of the present invention (e.g., PCT Publication Nos. WO 01/57118, WO 99/35520). These layer-by-layer techniques effectively alter the surfaces of various materials, such as contact lenses. One layer-by-layer (LbL) coating technique involves consecutively dipping a substrate into oppositely charged polymeric materials until a coating of a desired thickness is formed. In addition, another technique that results in a layer-by-layer coating while avoiding the time-consuming aspects of sequential dipping, is the single dip process disclosed in co-pending U.S. patent application Ser. No. 60/180,463 filed on Feb. 4, 2000, entitled "Single-Dip Process for Achieving a Layer-by-Layer-Like Coating", which applies charged polymeric material onto the substrate with only a single dip. In this technique, a generally hydrophobic article such as a contact lens is dipped into a single charged polymeric solution containing at least one polycationic material and at least one polyanionic material. The polycationic material may include a positively charged moiety such as poly(allyl amine hydrochloride) and the polyanionic material may include a negatively charged moiety such as polyacrylic acid. Typically, the charged polymeric components are employed in non-stoichiometric amounts such that one of the components is present within the solution in a greater amount than another component.

Each of these LbL-coating techniques is effective for producing an article with a surface that is different from the remainder of the article. However, these LbL-coating techniques require at least two oppositely charged polymeric materials and an article having an LbL coating produced therefrom may have a highly charged surface. A contact lens having a highly charged surface may be susceptible to the depositions of some proteins on the lens surface and/or may cause undesirable adverse effects on the wearer's comfort and/or ocular health. Therefore, it would be desirable if an LbL-coating process can be developed to produce coated articles having a significantly decreased charge density.

SUMMARY OF THE INVENTION

One object of the invention is to provide a method for making a polymeric article with a biocompatible LbL coating which comprises at least one charge/non-charge bilayer, wherein said charge/non-charge bilayer is composed of, in no particular order, one layer of a charged polymeric material and one layer of a non-charged polymeric material which is capable of being non-covalently bonded to the charged polymeric material.

Another object of the invention is to provide a polymeric articles with a biocompatible LbL coating which has a relatively low charge density and a relatively high hydrophilicity and lubricity.

These and other objects of the invention are met by the various aspects of the invention described herein.

The invention, in one aspect, provides a polymeric article, preferably an ophthalmic device, more preferably a contact lens, having a biocompatible LbL coating which comprises at least one charge/non-charge bilayer, wherein said charge/non-charge bilayer is composed of, in no particular order, one layer of a charged polymeric material and one layer of a non-charged polymeric material which is capable of being non-covalently bonded to the charged polymeric material.

The invention, in another aspect, provides a method of making a polymeric article, preferably, an ophthalmic device, more preferably a contact lens, having a biocompatible LbL coating, wherein the biocompatible LbL coating comprises at least one charge/non-charge bilayer, wherein said charge/non-charge bilayer is composed of, in no particular order, one layer of a charged polymeric material and one layer of a non-charged polymeric material which is capable of being non-covalently bonded to the charged polymeric material. The method of invention comprises alternatively applying one layer of a charged polymeric material and one layer of a non-charged polymeric material onto the surface of a polymeric article.

These and other aspects of the invention will become apparent from the following description of the presently preferred embodiments. The detailed description is merely illustrative of the invention and does not limit the scope of the invention, which is defined by the appended claims and equivalents thereof. As would be obvious to one skilled in the art, many variations and modifications of the invention may be effected without departing from the spirit and scope of the novel concepts of the disclosure.

DETAILED DESCRIPTION OF PREFERRED EMBODIMENTS

Reference now will be made in detail to the embodiments of the invention, one or more examples of which are set forth below. Each example is provided by way of explanation of the invention, and is not a limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention covers such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention.

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. As employed throughout the disclosure, the following terms, unless otherwise indicated, shall be understood to have the following meanings.

An "article" refers to a medical device or a mold for making a medical device.

A "medical device", as used herein, refers to a device having surfaces that contact tissue, blood, or other bodily fluids of patients in the course of their operation or utility. Exemplary medical devices include: (1) extracorporeal devices for use in surgery such as blood oxygenators, blood pumps, blood sensors, tubing used to carry blood and the like which contact blood which is then returned to the patient; (2) prostheses implanted in a human or animal body such as vascular grafts, stents, pacemaker leads, heart valves, and the like that are implanted in blood vessels or in the heart; (3) devices for temporary intravascular use such as catheters, guide wires, and the like which are placed into blood vessels or the heart for purposes of monitoring or repair; and (4) ophthalmic devices. In a preferred embodiment, medical devices are ophthalmic devices.

An "ophthalmic device", as used herein, refers to a contact lens (hard or soft), an intraocular lens, a corneal onlay, other ophthalmic devices (e.g., stents, or the like) used on or about the eye or ocular vicinity, cases or containers for storing ophthalmic devices or ophthalmic solutions.

"biocompatible", as used herein, refers to a material or surface of a material, which may be in intimate contact with tissue, blood, or other bodily fluids of a patient for an extended period of time without significantly damaging the ocular environment and without significant user discomfort.

"Ophthalmically compatible", as used herein, refers to a material or surface of a material which may be in intimate contact with the ocular environment for an extended period of time without significantly damaging the ocular environment and without significant user discomfort. Thus, an ophthalmically compatible contact lens will not produce significant corneal swelling, will adequately move on the eye with blinking to promote adequate tear exchange, will not have substantial amounts of protein or lipid adsorption, and will not cause substantial wearer discomfort during the prescribed period of wear.

"Ocular environment", as used herein, refers to ocular fluids (e.g., tear fluid) and ocular tissue (e.g., the cornea)

which may come into intimate contact with a contact lens used for vision correction, drug delivery, wound healing, eye color modification, or other ophthalmic applications.

A "monomer" means a low molecular weight compound that can be polymerized. Low molecular weight typically means average molecular weights less than 700 Daltons.

A "macromer" refers to a medium and high molecular weight compound or polymer that contains functional groups capable of further polymerization. Medium and high molecular weight typically means average molecular weights greater than 700 Daltons.

"Polymer" means a material formed by polymerizing one or more monomers.

"Surface modification", as used herein, means that an article has been treated in a surface treatment process (or a surface modification process), in which, by means of contact with a vapor or liquid, and/or by means of application of an energy source (1) a coating is applied to the surface of an article, (2) chemical species are adsorbed onto the surface of an article, (3) the chemical nature (e.g., electrostatic charge) of chemical groups on the surface of an article are altered, or (4) the surface properties of an article are otherwise modified. Exemplary surface treatment processes include, but are not limited to, a surface treatment by energy (e.g., a plasma, a static electrical charge, irradiation, or other energy source), chemical treatments, the grafting of hydrophilic monomers or macromers onto the surface of an article, and layer-by-layer deposition of polyelectrolytes. A preferred class of surface treatment processes are plasma processes, in which an ionized gas is applied to the surface of an article. Plasma gases and processing conditions are described more fully in U.S. Pat. Nos. 4,312,575 and 4,632,844, which are incorporated herein by reference. The plasma gas is preferably a mixture of lower alkanes and nitrogen, oxygen or an inert gas.

"LbL coating", as used herein, refers to a coating obtained by a layer-by-layer ("LbL") alternative, physical deposition of two oppositely charged polymeric materials or of a charged polymeric material and a non-charged polymeric materials on an article. In an LbL coating, each layer of a material is non-covalently bond to another layer of a different material. Any suitable deposition techniques can be used in the LbL coating. Exemplary deposition techniques include, without limitation, dipping a substrate into a coating solution and spraying a substrate with a coating solution. A "charged polymeric material" or a polyionic material refers to a charged polymer that has a plurality of charged groups in a solution, or a mixture of charged polymers each of which has a plurality of charged groups in a solution. Exemplary charged polymers includes polyelectrolytes, p- and n-type doped conducting polymers. Charged polymeric materials include both polycationic (having positive charges) and polyanionic (having negative charges) polymeric materials.

The term "bilayer" is employed herein in a broad sense and is intended to encompass, a coating structure formed by alternatively applying, in no particular order, one layer of a first charged polymeric material and one layer of a non-charged polymeric material or a second charged polymeric material. It should be understood that the layers of the first charged polymeric material and the non-charged polymeric material (or second charged polymeric material) may be intertwined with each other in the bilayer.

An "innermost layer", as used herein, refers to the first layer of an LbL coating, which is applied onto the surface of a medical device.

A "capping layer", as used herein, refers to the last layer of an LbL coating which is applied onto the surface of a medical device.

A "polyquat", as used herein, refers to a polymeric quaternary ammonium group-containing compound.

An "averaged value of coefficient of friction" refers to a value, which is obtained by averaging measurements of at least 3 individual medical devices, as described in Example 10. Coefficient of friction (hereinafter CoF) may be one of important parameters that may affect the on-eye movement and thereby the wearer's comfort. High CoF may increase the likelihood of damaging mechanically the ocular epithelia and/or may lead to ocular discomfort.

As used herein, "increased lubricity" in reference to a coated medical device, e.g., a coated contact lens, means that the medical device has a reduced averaged value of CoF relative to an uncoated medical device, wherein both coated and uncoated medical device are made of the same core material.

An "average contact angle" refers to a contact angle (measured by Sessile Drop method), which is obtained by averaging measurements of at least 3 individual medical devices.

As used herein, "increased surface hydrophilicity" or "increased hydrophilicity" in reference to a coated ophthalmic device means that the coated ophthalmic device has a reduced averaged contact angle relative to an uncoated medical device, wherein both coated and uncoated medical device are made of the same core material.

The present invention, in one aspect, provides a method for producing a medical device having a core material and a biocompatible LbL coating comprising at least one layer of a charged polymeric material and one layer of a non-charged polymeric material which can be non-covalently bonded to the charged polymeric material. The method of the invention comprises contacting alternatively, in no particular order, with a solution of a charged polymeric material to form one layer of the charged polymeric material and with a solution of a non-charged polymeric material, which can be bond non-covalently to the charged polymeric material, to form one layer of the non-charged polymeric material.

It has been discovered previously and disclosed in U.S. application Ser. No. 09/005,317 that complex and time-consuming pretreatment of a core material (medical device) is not required prior to binding of a charged polymeric material to the core material. By simply and alternatively contacting a core material of a medical device, for example, a contact lens, with a solution of a first charged polymeric material and a solution of a second charged polymeric material having charges opposite of the charges of the first charged polymeric material, a multiple-layered LbL coating can be formed on a medical device to modify the surface properties of the core material of the medical device.

It has been discovered here that one layer of a charged polymeric material and one layer of a non-charged polymeric material, which replaces one of the two oppositely-charged polymeric materials, can be alternatively deposited onto a substrate to form a biocompatible LbL coating, according to an unknown mechanism. Such coating can provide a relatively low surface charge density. It was quite unexpected to find that the polymeric material which does not contain any charged groups can also be physically (i.e., non-covalently) bonded to the charged polymeric material to create a multi-layered wear-resistant LbL coating on a substrate. While the claimed invention is not limited to the theory developed to support this unexpected result, a proposed theory is presented herein in order to enable the reader to better understand the invention. It is believed that there may exist some molecular interactions between the charged groups of the charged polymeric material and the non-charged functional groups of the non-charged polymeric material so that complexation/precipitation of a layer of the non-charged polymeric material may occurs on the layer of the charged polymeric material on a substrate.

The non-charged polymeric material according to the invention can be: a homopolymer of a vinyl lactam; a copolymer of at least one vinyl lactam in the presence or in the absence of one or more hydrophilic vinylic comonomers; or mixtures thereof.

The vinyl lactam has a structure of formula (I)

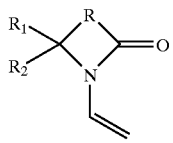

(I)

wherein
R is an alkylene di-radical having from 2 to 8 carbon atoms,
$R_1$ is hydrogen, alkyl, aryl, aralkyl or alkaryl, preferably hydrogen or lower alkyl having up to 7 and, more preferably, up to 4 carbon atoms, such as, for example, methyl, ethyl or propyl;
aryl having up to 10 carbon atoms, and also aralkyl or alkaryl having up to 14 carbon atoms; and
$R_2$ is hydrogen or lower alkyl having up to 7 and, more preferably, up to 4 carbon atoms, such as, for example, methyl, ethyl or propyl.

Some N-vinyl lactams corresponding to the above structural formula (I) are N-vinyl-2-pyrrolidone, N-vinyl-2-piperidone, N-vinyl-2-caprolactam, N-vinyl-3-methyl-2-pyrrolidone, N-vinyl-3-methyl-2-piperidone, N-vinyl-3-methyl-2-caprolactam, N-vinyl-4-methyl-2-pyrrolidone, N-vinyl-4-methyl-2-caprolactam, N-vinyl-5-methyl-2-pyrrolidone, N-vinyl-5-methyl-2-piperidone, N-vinyl-5,5-dimethyl-2-pyrrolidone, N-vinyl-3,3,5-trimethyl-2-pyrrolidone, N-vinyl-5-methyl-5-ethyl-2-pyrrolidone, N-vinyl-3,4,5-trimethyl-3-ethyl-2-pyrrolidone, N-vinyl-6-methyl-2-piperidone, N-vinyl-6-ethyl-2-piperidone, N-vinyl-3,5-dimethyl-2-piperidone, N-vinyl-4,4-dimethyl-2-piperidone, N-vinyl-7-methyl-2-caprolactam, N-vinyl-7-ethyl-2-caprolactam, N-vinyl-3,5-dimethyl-2-caprolactam, N-vinyl-4,6-dimethyl-2-caprolactam and N-vinyl-3,5,7-trimethyl-2-caprolactam.

A preferred non-charged polymeric material is a polymer, copolymer derived from a vinyl lactam which is a heterocyclic monomer of formula (I) containing from 4 to 6 carbon atoms in the heterocyclic ring, or a mixture thereof.

A more preferred non-charged polymeric material is a polymer, copolymer derived from a vinyl lactam which is a heterocyclic monomer of formula (I) containing 4 carbon atoms in the heterocyclic ring, or a mixture thereof.

An even more preferred non-charged polymeric material is a polymer, copolymer derived from a vinyl lactam which is a heterocyclic monomer of formula (I) containing 4 carbon atoms in the heterocyclic ring and wherein $R_1$ and $R_2$ are each independently of the other hydrogen or lower alkyl, or a mixture thereof.

A most preferred non-charged polymeric material is a polymer, copolymer derived from a vinyl lactam, which is N-vinyl-2-pyrrolidone, or a mixture thereof.

Suitable hydrophilic vinylic comonomers include, without limitation, hydroxy-substituted lower alkylacrylates and -methacrylates, acrylamide, methacrylamide, lower alkyl-acrylamides and -methacrylamides, ethoxylated acrylates and methacrylates, hydroxy-substituted lower alkyl-acrylamides and -methacrylamides, hydroxy-substituted lower alkylvinyl-ethers, sodium ethylene sulphonate, sodium styrene sulphonate, 2-acrylamido-2-methyl-propane-sulphonic acid, N-vinyl pyrrole, N-vinyl succinimide, N-vinyl pyrrolidone, 2- or 4-vinyl pyridine, acrylic acid, methacrylic acid, amino-(whereby the term "amino" also includes quaternary ammonium), mono-lower-alkylamino-or di-lower-alkylamino-lower-alkyl-acrylates and -methacrylates, allyl alcohol and the like. Preference is given e.g. to hydroxy-substituted $C_2$–$C_4$-alkyl(meth) acrylates, five- to seven-membered N-vinyl-lactams, N,N-di-$C_1$–$C_4$-alkyl-methacrylamides and vinylically unsaturated carboxylic acids with a total of 3 to 5 carbon atoms.

Where a homopolymer of a vinyl lactam; a copolymer of at least one vinyl lactam in the presence or in the absence of one or more hydrophilic vinylic comonomers; or mixtures thereof is used as a non-charged polymeric material to build-up charge/non-charge bilayers of the invention, a charged polymeric material is preferably a polyanionic polymer or a mixture of polyanionic polymer. Examples of suitable polyanionic polymers include, for example, a synthetic polymer, a biopolymer or modified biopolymer comprising carboxy, sulfo, sulfato, phosphono or phosphato groups or mixtures thereof, or a salt thereof, for example, a biomedical acceptable salt and especially an ophthalmically acceptable salt thereof when the article to be coated is an ophthalmic device.

Examples of synthetic polyanionic polymers are: a linear polyacrylic acid (PAA), a branched polyacrylic acid, a polymethacrylic acid (PMA), a polyacrylic acid or polymethacrylic acid copolymer, a maleic or fumaric acid copolymer, a poly(styrenesulfonic acid) (PSS), a polyamido acid, a carboxy-terminated polymer of a diamine and a di- or polycarboxylic acid (e.g., carboxy-terminated Starburst™ PAMAM dendrimers from Aldrich), a poly(2-acrylamido-2-methylpropanesulfonic acid) (poly-(AMPS)), an alkylene polyphosphate, an alkylene polyphosphonate, a carbohydrate polyphosphate or carbohydrate polyphosphonate (e.g., a teichoic acid). Examples of a branched polyacrylic acid include a Carbophil® or Carbopol® type from Goodrich Corp. Examples of a copolymer of acrylic or methacrylic acid include a copolymerization product of an acrylic or methacrylic acid with a vinylmonomer including, for example, acrylamide, N,N-dimethyl acrylamide or N-vinylpyrrolidone.

Examples of polyanionic biopolymers or modified biopolymers are: hyaluronic acid, glycosaminoglycanes such as heparin or chondroitin sulfate, fucoidan, poly-aspartic acid, poly-glutamic acid, carboxymethyl cellulose, carboxymethyl dextranes, alginates, pectins, gellan, carboxyalkyl chitins, carboxymethyl chitosans, sulfated polysaccharides.

A preferred polyanionic polymer is a linear or branched polyacrylic acid or an acrylic acid copolymer. A more preferred anionic polymer is a linear or branched polyacrylic acid. A branched polyacrylic acid in this context is to be understood as meaning a polyacrylic acid obtainable by polymerizing acrylic acid in the presence of suitable (minor) amounts of a di- or polyvinyl compound.

A suitable polycationic polymer as part of the bilayer is, for example, a synthetic polymer, biopolymer or modified biopolymer comprising primary, secondary or tertiary amino groups or a suitable salt thereof, preferably an ophthalmically acceptable salt thereof, for example a hydrohalogenide such as a hydrochloride thereof, in the backbone or as substituents.

Polycationic polymers comprising primary or secondary amino groups or a salt thereof are preferred.

Examples of synthetic polycationic polymers are:
(i) a polyallylamine (PAH) homo- or copolymer, optionally comprising modifier units;
(ii) a polyethyleneimine (PEI);
(iii) a polyvinylamine homo- or copolymer, optionally comprising modifier units;
(iv) a poly(vinylbenzyl-tri-$C_1$–$C_4$-alkylammonium salt), for example a poly(vinylbenzyl-tri-methyl ammoniumchloride);
(v) a polymer of an aliphatic or araliphatic dihalide and an aliphatic N,N,N',N'-tetra-$C_1$–$C_4$-alkyl-alkylenediamine, for example a polymer of (a) propylene-1,3-dichloride or -dibromide or p-xylylene dichloride or dibromide and (b) N,N,N',N'-tetramethyl-1,4-tetramethylene diamine;
(vi) a poly(vinylpyridine) or poly(vinylpyridinium salt) homo- or copolymer;
(vii) a poly (N,N-diallyl-N,N-di-$C_1$–$C_4$-alkyl-ammoniumhalide) comprising units of formula

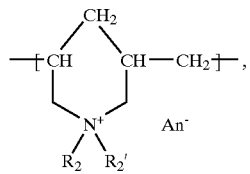

wherein $R_2$ and $R_2'$ are each independently $C_1$–$C_4$-alkyl, in particular methyl, and $An^-$ is an anion, for example, a halide anion such as the chloride anion;
(viii) a homo- or copolymer of a quaternized di-$C_1$–$C_4$-alkyl-aminoethyl acrylate or methacrylate, for example a poly(2-hydroxy-3-methacryloylpropyltri-$C_1$–$C_2$-alkylammonium salt) homopolymer such as a poly(2-hydroxy-3-methacryloylpropyltri-methylammonium chloride), or a quaternized poly(2-dimethylaminoethyl methacrylate or a quaternized poly(vinylpyrrolidone-co-2-dimethylaminoethyl methacrylate);
(ix) POLYQUAD® as disclosed in EP-A-456,467; or
(x) a polyaminoamide (PAMAM), for example a linear PAMAM or a PAMAM dendrimer such as an amino-terminated Starbust™ PAMAM dendrimer (Aldrich).

The above mentioned polymers comprise in each case the free amine, a suitable salt thereof, for example a biomedically acceptable salt or in particular an ophthalmically acceptable salt thereof, as well as any quaternized form, if not specified otherwise.

Suitable comonomers optionally incorporated in the polymers according to (i), (iii), (vi) or (viii) above are, for example, hydrophilic monomers such as acrylamide, methacrylamide, N,N-dimethyl acrylamide, N-vinylpyrrolidone and the like.

Suitable modifier units of the polyallylamine (i) are known, for example from WO 00/31150 and comprise, for example, units of formula

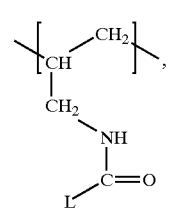

wherein L is $C_2$–$C_6$-alkyl, which is substituted by two or more same, or different substituents selected from the group consisting of hydroxy, $C_2$–$C_5$-alkanoyloxy and $C_2$–$C_5$-alkylamino-carbonyloxy.

Preferred substituents of the alkyl radical L are hydroxy, acetyloxy, propionyloxy, methyl-aminocarbonyloxy or ethylaminocarbonyloxy, especially hydroxy, acetyloxy or propionyloxy and in particular hydroxy.

L is preferably linear $C_3$–$C_6$-alkyl, more preferably linear $C_4$–$C_5$-alkyl, and most preferably n-pentyl, which is in each case substituted as defined above. A particularly preferred radical L is 1,2,3,4,5-pentahydroxy-n-pentyl.

Examples of polycationic biopolymers or modified biopolymers that may be employed in the bilayer of the present invention include: basic peptides, proteins or glucoproteins, for example, a poly-ε-lysine, albumin or collagen, aminoalkylated polysaccharides such as a chitosan or aminodextranes.

Particular polycationic polymers for forming the bilayer of the present invention include a polyallylamine homopolymer; a polyallylamine comprising modifier units of the above formula (II); a polyvinylamine homo- or -copolymer or a polyethyleneimine homopolymer, in particular a polyallylamine or polyethyleneimine homopolymer, or a poly (vinylamine-co-acrylamid) copolymer.

The foregoing lists are intended to be exemplary, but clearly are not exhaustive. A person skilled in the art, given the disclosure and teaching herein, would be able to select a number of other useful charged polymeric materials.

In order to alter various characteristics of the coating, such as thickness, the molecular weight of the charged polymeric materials and non-charged polymeric materials can be varied. In particular, as the molecular weight is increased, the coating thickness generally increases. However, if the increase in molecular weight increase is too substantial, the difficulty in handling may also increase. As such, coating materials including charged polymeric and non-charged polymeric materials used in a process of the present invention will typically have a molecular weight $M_n$ of about 2,000 to about 150,000. In some embodiments, the molecular weight is about 5,000 to about 100,000, and in other embodiments, from about 75,000 to about 100,000.

In accordance with the present invention, the core material of a medical device may be any of a wide variety of polymeric materials. Exemplary core materials include, but are not limited to, hydrogels, silicone-containing hydrogels, polymers and copolymers of styrene and substituted styrenes, ethylene, propylene, acrylates and methacrylates, N-vinyl lactams, acrylamides and methacrylamides, acrylonitrile, acrylic and methacrylic acids.

A preferred group of core materials to be coated are those being conventionally used for the manufacture of biomedical devices, e.g. contact lenses, in particular contact lenses for extended wear, which are not hydrophilic per se. Such materials are known to the skilled artisan and may comprise for example polysiloxanes, perfluoroalkyl polyethers, fluorinated poly(meth)acrylates or equivalent fluorinated polymers derived e.g. from other polymerizable carboxylic acids, polyalkyl (meth)acrylates or equivalent alkylester polymers derived from other polymerizable carboxylic acids, or fluorinated polyolefines, such as fluorinated ethylene or propylene, for example tetrafluoroethylene, preferably in combination with specific dioxols, such as perfluoro-2,2-dimethyl-1,3-dioxol. Examples of suitable bulk materials are e.g. Lotrafilcon A, Neofocon, Pasifocon, Telefocon, Silafocon, Fluorsilfocon, Paflufocon, Silafocon, Elastofilcon, Fluorofocon or Teflon AF materials, such as Teflon AF 1600 or Teflon AF 2400 which are copolymers of about 63 to 73 mol % of perfluoro-2,2-dimethyl-1,3-dioxol and about 37 to 27 mol % of tetrafluoroethylene, or of about 80 to 90 mol % of perfluoro-2,2-dimethyl-1,3-dioxol and about 20 to 10 mol % of tetrafluoroethylene.

Another group of preferred core materials to be coated is amphiphilic-segmented copolymers comprising at least one hydrophobic segment and at least one hydrophilic segment, which are linked through a bond or a bridge member. Examples are silicone hydrogels, for example those disclosed in PCT applications WO 96/31792 to Nicolson et al. and WO 97/49740 to Hirt et al.

A particular preferred group of core materials to be coated comprises organic polymers selected from polyacrylates, polymethacrylates, polyacrylamides, poly(N,N-dimethylacrylamides), polymethacrylamides, polyvinyl acetates, polysiloxanes, perfluoroalkyl polyethers, fluorinated polyacrylates or -methacrylates and amphiphilic segmented copolymers comprising at least one hydrophobic segment, for example a polysiloxane or perfluoroalkyl polyether segment or a mixed polysiloxane/perfluoroalkyl polyether segment, and at least one hydrophilic segment, for example a polyoxazoline, poly(2-hydroxyethylmethacrylate), polyacrylamide, poly(N,N-dimethylacrylamide), polyvinylpyrrolidone polyacrylic or polymethacrylic acid segment or a copolymeric mixture of two or more of the underlying monomers.

The core material to be coated may also be any blood-contacting material conventionally used for the manufacture of renal dialysis membranes, blood storage bags, pacemaker leads or vascular grafts. For example, the material to be modified on its surface may be a polyurethane, polydimethylsiloxane, polytetrafluoroethylene, polyvinylchloride, Dacron™ or Silastic™ type polymer, or a composite made therfrom.

The contacting of the medical device with a solution of, either a charged polymeric material, a non-charged polymeric material or a rinsing solution, may occur by a variety of methods. For example, the medical device may be dipped into a solution. Alternatively, the medical device is sprayed with a solution in a spray or mist form. One coating process embodiment involves solely dip-coating and optionally dip-rinsing steps. Another coating process embodiment involves solely spray-coating and optionally spray-rinsing steps. Of course, a number of alternatives involve various combinations of spray- and dip-coating and optionally spray- and dip-rinsing steps may be designed by a person having ordinary skill in the art.

For example, a solely dip-coating process involves the steps of: immersing a medical device in a solution of a charged polymeric material; optionally rinsing the medical device by immersing the medical device in a rinsing solution; immersing said medical device in a solution of a non-charged polymeric material which can be non-covalently bond to the charged polymeric material on the medical device; and optionally rinsing said medical device in a rinsing solution, thereby to form a bilayer of the charged polymeric material and the non-charged polymeric material. This bilayer formation process may be repeated a plurality of times in order to produce a thicker LbL coating.

The immersion time for each of the coating and optional rinsing steps may vary depending on a number of factors. Preferably, immersion of the core material into a coating solution occurs over a period of about 1 to 30 minutes, more preferably about 1 to 20 minutes, and most preferably about 1 to 5 minutes. Rinsing may be accomplished with a plurality of rinsing steps, but a single rinsing step, if desired, can be quite efficient.

Another embodiment of the coating process involves a series of spray coating techniques. The process generally includes the steps of: spraying a core material of a medical device with a solution of a charged polymeric material; optionally rinsing the medical device by spraying the medical device with a rinsing solution and then optionally drying the medical device; spraying the medical device with a solution of a non-charged polymeric material which can be non-covalently bond to the charged polymeric material on the medical device; optionally rinsing the medical device by spraying the medical device with a rinsing solution, thereby to form a bilayer of the charged polymeric material and the non-charged polymeric material. This bilayer formation procedure may be repeated a plurality of times in order to produce a thicker LbL coating.

The spray coating application may be accomplished via a process selected from the group consisting of an air-assisted atomization and dispensing process, an ultrasonic-assisted atomization and dispensing process, a piezoelectric assisted atomization and dispensing process, an electro-mechanical jet printing process, a piezo-electric jet printing process, a piezo-electric with hydrostatic pressure jet printing process, and a thermal jet printing process; and a computer system capable of controlling the positioning of the dispensing head of the spraying device on the ophthalmic lens and dispensing the coating liquid. Those spraying coating processes are described in U.S. application Ser. No. 60/312,199, herein incorporated by reference in its entirety. By using such spraying coating processes, an asymmetrical coating can be applied to a medical device. For example, the back surface of a contact lens can be coated with a hydrophilic and/or lubricous coating material and the front surface of the contact lens can be coated with an antimicrobial material. It is also possible to produce a coating on a contact lens, the coating having a functional pattern so as to provide simultaneously multiple benefits to a wearer.

A preferred number of bilayers in a biocompatible LbL coating of the invention are about 5 to about 20 bilayers. While more than 20 bilayers are possible, it has been found that delamination may occur in some LbL coatings having an excessive number of bilayers.

A biocompatible LbL coating of the invention can comprise at least one layer of a first charged polymeric material and at least one layer of a second charged polymeric material, wherein the first and second charged polymeric material have the same sign of charges.

A biocompatible LbL coating of the invention can comprise at least one layer of a first non-charged materials and at least one layer of a second non-charged polymeric material, wherein each of the first and second non-charged polymeric materials can be bond non-covalently to adjacent layers of a charged polymeric material.

A biocompatible LbL coating of the invention can comprise one or more bilayers of a first charged polymeric material and a second charged polymeric material having charges opposite of the charges of the first charged polymeric material.

In accordance with the present invention, coating solutions can be prepared in a variety of ways. In particular, a coating solution of the present invention can be formed by dissolving a charged polymeric material or a non-charged polymeric material in water or any other solvent capable of dissolving the materials. When a solvent is used, any solvent that can allow the components within the solution to remain stable in water is suitable. For example, an alcohol-based solvent can be used. Suitable alcohol can include, but are not limited to, isopropyl alcohol, hexanol, ethanol, etc. It should be understood that other solvents commonly used in the art can also be suitably used in the present invention.

Whether dissolved in water or in a solvent, the concentration of a coating material (i.e., a charged polymeric material or a non-charged polymeric material) in a solution of the present invention can generally vary depending on the particular materials being utilized, the desired coating thickness, and a number of other factors.

It may be typical to formulate a relatively dilute aqueous solution of charged polymeric material. For example, a charged polymeric material concentration can be between about 0.0001% to about 0.25% by weight, between about 0.005% to about 0.10% by weight, or between about 0.01% to about 0.05% by weight.

However, where a coating solution containing a first charged polymeric material is used to form an innermost layer of a biocompatible LbL coating of the invention on the surface of a medical device, it is desirable that the concentration of the first charged polymeric material in the solution is sufficiently high enough to increase the hydrophilicity of the LbL coating. It is discovered that the concentration of a charged polymeric material in a solution for forming the innermost layer of an LbL coating has a direct significant impact on the hydrophilicity of the LbL coating on a contact lens. When the concentration of the charged polymeric material increases, the hydrophilicity of the LbL coating increases. Preferably, the concentration of the charged polymeric material in a solution for forming the innermost layer of an LbL coating is at least three folder higher than the concentration of a coating material in a coating solution for forming subsequent layers of the LbL coating. More preferably, the concentration of the charged polymeric material in a solution for forming the innermost layer of an LbL coating is at least ten folder higher than the concentration of a coating material in a coating solution for forming subsequent layers of the LbL coating.

In general, the charged polymeric solutions mentioned above can be prepared by any method well known in the art for preparing solutions. For example, in one embodiment, a polyanionic solution can be prepared by dissolving a suitable amount of the polyanionic material, such as polyacrylic acid having a molecular weight of about 90,000, in water such that a solution having a certain concentration is formed. In one embodiment, the resulting solution is a 0.001M PAA solution. Once dissolved, the pH of the polyanionic solution can also be adjusted by adding a basic or acidic material. In the embodiment above, for example, a suitable amount of 1N hydrochloric acid (HCl) can be added to adjust the pH to 2.5.

Solutions of a polycationic material or non-charged polymeric material can also be formed in a manner as described above. For example, in one embodiment, poly(allylamine hydrochloride) having a molecular weight of about 50,000 to about 65,000 can be dissolved in water to form a 0.001M PAH solution. Thereafter, the pH can also be adjusted to 2.5 by adding a suitable amount of hydrochloric acid.

In some embodiments of the invention, the coating process for forming a biocompatible LbL coating on a medical device comprises: applying, directly onto the core material of a medical device, one or more bilayer of a first charged polymeric material and a second charged polymeric material having charges opposite of the charges of the first charged polymeric material; and then applying one or more bilayers of the first (or second) charged polymeric material and a non-charged polymeric material which can be non-covalently bond to the first (or second) charged polymeric material.

Where a biocompatible LbL coating comprises at least one bilayer of a first charged polymeric material and a second charged polymeric material having charges opposite of the charges of the first charged polymeric material, it may be desirable to apply a solution containing both the first and second charged polymeric materials within a single solution. For example, a polyanionic solution can be formed as described above, and then mixed with a polycationic solution that is also formed as described above. The solutions can then be mixed slowly to form a coating solution. The amount of each solution applied to the mix depends on the molar charge ratio desired. For example, if a 10:1 (polyanion:polycation) solution is desired, 1 part (by volume) of the PAH solution can be mixed into 10 parts of the PAA solution. After mixing, the solution can also be filtered if desired.

An LbL coating of the present invention may find particular use in extended-wear contact lenses. The LbL coating of the invention may have a minimal adverse effects on the desirable bulk properties of the lens, such as oxygen permeability, ion permeability, and optical properties.

The present invention, in another aspect, provides a medical device having a core material and an LbL coating formed thereon and a surface hydrophilicity characterized by having an average contact angle of about 80 degrees or less, wherein the LbL coating comprises at least one bilayer composed of one layer of a charged polymeric material and one layer of a non-charged polymeric material which can be non-covalently bonded to the charged polymeric material. Preferably, the coated medical device has an increased lubricity characterized by an average CoF of about 3.5 or less.

A medical device of the invention can be made by applying a biocompatible LbL coating to a preformed medical device according to an above-described method of the invention.

A medical device of the invention can also be made by first applying a biocompatible LbL coating to a mold for making a medical device and then transfer-grafting the biocompatible LbL coating to the medical device made from the mold, in substantial accordance with the teachings of U.S. patent application (Ser. No. 09/774,942), herein incorporated by reference in its entirety.

Methods of forming mold sections for cast-molding a contact lens are generally well known to those of ordinary skill in the art. The process of the present invention is not limited to any particular method of forming a mold. In fact, any method of forming a mold can be used in the present invention. However, for illustrative purposes, the following discussion has been provided as one embodiment of forming a transferable biocompatible LbL coating on a mold and then making a contact lens with a biocompatible LbL coating thereon from the coated mold in accordance with the present invention.

In general, a mold comprises at least two mold sections (or portions) or mold halves, i.e. first and second mold halves. The first mold half defines a first optical surface and the second mold half defines a second optical surface. The first and second mold halves are configured to receive each other such that a contact lens forming cavity is formed between the first optical surface and the second optical surface. The first and second mold halves can be formed through various techniques, such as injection molding. These half sections can later be joined together such that a contact lens-forming cavity is formed therebetween. Thereafter, a contact lens can be formed within the contact lens-forming cavity using various processing techniques, such as ultraviolet curing.

Examples of suitable processes for forming the mold halves are disclosed in U.S. Pat. Nos. 4,444,711 to Schad; 4,460,534 to Boehm et al.; 5,843,346 to Morrill; and 5,894,002 to Boneberger et al., which are also incorporated herein by reference.

Virtually all materials known in the art for making molds can be used to make molds for making contact lenses. For example, polymeric materials, such as polyethylene, polypropylene, and PMMA can be used. Other materials that allow UV light transmission could be used, such as quartz glass.

Once a mold is formed, a transferable biocompatible LbL coating, which comprises at least one bilayer of a charged polymeric material and a non-charged polymeric material, can be applied onto the optical surface (inner surface) of one or both mold portions by using the above-described LbL deposition techniques. The inner surface of a mold portion is the cavity-forming surface of the mold and in direct contact with lens-forming material. A transferable biocompatible LbL coating can be applied onto the mold portion defining the posterior (concave) surface of a contact lens or on the mold section defining the anterior surface of a contact lens or on both mold portions.

Once a transferable biocompatible LbL coating is applied onto the optical surface of one or both mold portions, a lens material can then be dispensed into the contact lens forming cavity defined by the assembled mold halves. In general, a lens material can be made from any polymerizable composition. In particular, when forming a contact lens, the lens material may be an oxygen-permeable material, such as fluorine- or siloxane-containing polymer. For example, some examples of suitable substrate materials include, but are not limited to, the polymeric materials disclosed in U.S. Pat. No. 5,760,100 to Nicolson et al., which is incorporated herein by reference. The lens material can then be cured, i.e. polymerized, within the contact lens-forming cavity to form the contact lens, whereby at least a portion of the transferable biocompatible LbL coating detaches from the optical surface and reattaches to the formed contact lens.

Thermal curing or photo curing methods can be used to curing a polymerizable composition in a mold to form an ophthalmic lens. Such curing methods are well-known to a person skilled in the art.

In addition to charged and non-charged polymeric materials, a coating solution for forming the bilayer or part of it, can also contain additives. As used herein, an additive can generally include any chemical or material. For example, active agents, such as antimicrobials and/or antibacterials can be added to a solution forming the bilayer, particularly when used in biomedical applications. Some antimicrobial charged polymeric materials include polyquaternary ammonium compounds, such as those described in U.S. Pat. No. 3,931,319 to Green et al. (e.g. POLYQUAD®).

Moreover, other examples of materials that can be added to a coating solution are materials useful for ophthalmic lenses, such as materials having radiation absorbing properties. Such materials can include, for example, visibility-tinting agents, iris color modifying dyes, and ultraviolet (UV) light tinting dyes.

Still another example of a material that can be added to a coating solution is a material that inhibits or induces cell growth. Cell growth inhibitors can be useful in devices that are exposed to human tissue for an extended time with an ultimate intention to remove (e.g. catheters or Intra Ocular Lenses (IOL's), where cell overgrowth is undesirable), while cell growth-inducing charged polymeric materials can be useful in permanent implant devices (e.g. artificial cornea).

When additives are applied to a coating solution, such additives, preferably, have a charge. By having a positive or negative charge, the additive can be substituted for the charged polymeric material in solution at the same molar ratio. For example, polyquaternary ammonium compounds typically have a positive charge. As such, these compounds can be substituted into a solution of the present invention for the polycationic component such that the additive is applied to the core material of an article in a manner similar to how a polycationic would be applied.

It should be understood, however, that non-charged additives can also be applied to the core material of an article by entrapment.

Moreover, the core material to be coated may also be an inorganic or metallic base material without suitable reactive groups, e.g. ceramic, quartz, or metals, such as silicon or gold, or other polymeric or non-polymeric substrates e.g., for implantable biomedical applications, ceramics are very useful. In addition, e.g. for biosensor purposes, hydrophilically coated base materials are expected to reduce nonspecific binding effects if the structure of the coating is well controlled. Biosensors may require a specific carbohydrate coating on gold, quartz, or other non-polymeric substrates.

The form of the material to be coated may vary within wide limits. Examples are particles, granules, capsules, fibers, tubes, films or membranes, preferably moldings of all kinds such as ophthalmic moldings, for example intraocular lenses, artificial cornea or in particular contact lenses.

The previous disclosure will enable one having ordinary skill in the art to practice the invention. In order to better enable the reader to understand specific embodiments and the advantages thereof, reference to the following examples is suggested.

EXAMPLE 1

Measurements of CoF of Coated Contact Lenses

COF may be one of parameters that measure the easiness of the on-eye movement of a contact lens. High CoF may increase the likelihood of damaging mechanically the ocular epithelia. CoF of a contact lens can be measured by a sled-on-block type of friction tester as follow. Under a certain load (e.g., about 2.0 grams), a contact lens is slid back and forth, at a prescribed speed, against a biologically relevant substrate and both the normal force (N) and the tangential force ($F_T$) are measured. The CoF of the contact lens is calculated based on the equation of $\mu = F_T/N$.

A preferred friction tester comprises: a stationary lens holder assembly, a biologically relevant substrate, a horizontally movable platform, and a plurality of force measuring means.

The stationary lens holder assembly preferably comprises an "A-shaped" holder bracket and a lens holder having a lens-supporting surface. The lens-supporting surface of the lens holder has a convex curvature capable of accommodating the back (concave) surface of a contact lens. The lens holder is preferably held by a means in the center of the "A-shaped" holder bracket. The head end of the "A-shaped" stationary sample holder bracket is connected to a first force measuring means (e.g., a load cell from Transducer Techniques) by, for example, a Kevlar® fiber. The two foot-ends of the "A-shaped" holder bracket are connected to nylon string attached with two ½" steel extension springs. The first force measuring means and the steel extension springs are mounted to the frame of the tester.

The horizontally movable platform can be, for example, a table platform (x-table) which moves uniaxially at various speeds and accelerations. The x-table preferably has a dimension of 163 mm long and 19.1 mm wide and can provide a test area having about 140 mm long and about 14.7 mm wide. An example of the x-table is a Model 41 Linear Positioner, which is powered by a ZETA Drive Compumotor (Parker Hannifin Corporation), which operates unidirectional at maximum velocities of 1800 mm/min and accelerations of 9000 mm/s$^2$.

The biologically relevant substrate can be any material and preferably is a powder-free surgical glove with Biogel® Coating® from Regent®. Preferably, the finger of the glove is cut into a single rectangular strip, and stretched and attached to the x-table by a physical means, for example, jumbo paper clips. Before testing, the substrate attached onto the x-table is lubricated with two drops of a desired lubricant, for example, ultra pure water or Softwear® saline (CIBA Vision). Any air between the substrate and the x-table should be removed. The desired lubricant should be applied evenly on the substrate. The substrate should be even and consistent throughout.

Preferably, there are three force-measuring means, a first, a second and a third force-measuring means. Any suitable known force measuring means can be used. An example is a 100-gram load cells from Transducer Techniques. The first force-measuring means is attached to the sample holder to measure tangential forces (friction forces, $F_T$) in two opposite directions. The second and third force measuring means reside under the x-table to measure normal force (N) in the downward direction. The other load cell Values outputted by the normal load cells are converted to grams by a Versatile Amplifier/Conditioner (Transducer Techniques).

Measurements of CoF are performed on the preferred friction tester as follows. A contact lens is placed on a lens holder with the back surface of the contact lens against the lens-supporting surface of the lens hold. The lens holder with the contact lens is assembled with the "A-shaped" holder bracket and then placed in contact with a desired lubricated substrate. This substrate is mounted to a horizontally movable table platform that is capable of moving uniaxially at various speeds and accelerations. About 3 grams of weight is loaded onto the lens holder. This load may represent the force pressed on a contact lens by a blink of eyelids. The three force-measuring means (3 Load cells from Transducer Techniques) measure simultaneously the normal (N) and frictional ($F_T$) forces that are produced from the interaction between the contact lens and the substrate lubricated with a desired lubricant. Multiple data points are taken during a measurement of lubricity/lubricating d rag/ coefficient of friction of a contact lens. At each data point, CoF $\mu$, is calculated as follows:

$$\mu = F_T/N$$

in which $F_T$ represent actual data reading at each point obtained by the first force measuring means after correcting for the preloading provided by the springs (tangential load cell) during sliding of the substrate against the contact lens and preferably has a unit of gram; N is the sum of $N_1$ and $N_2$; N1 represents actual data reading at each point obtained by the second force-measuring means after correcting for any preloading by the test assembly (normal load cell#1) during sliding of substrate against the contact lens and preferably has a unit of gram; and $N_2$ represents actual data reading at each point obtained by the third force-measuring means after correcting for any preloading by the test assembly (normal load cell#2) during sliding of substrate against the contact lens and has preferably a unit of gram. The average ($\mu_{Ave}$) of all $\mu$'s at every data point will be used to represent the value of CoF of a contact lens.

More preferably, the friction tester further comprises a computer system that controls the tester, collects readings of the normal and tangential forces simultaneously as the biologically-relevant substrate interacts with contact lens, calculates CoF, and records and charts the forces ($F_T$ and N) and CoF ($\mu$) at each data point during testing.

EXAMPLE 2

Measurements of Contact Angles of Coated Contact Lenses

Average contact angles (Sessile Drop) of contact lenses are measured using a VCA 2500 XE contact angle measurement device from AST, Inc., located in Boston, Mass. This equipment is capable of measuring advancing or receding contact angles or sessile (static) contact angles. The measurements are preferably performed on fully hydrated materials.

The contact angle is a general measure of the surface hydrophilicity of a contact lens. In particular, a low contact angle corresponds to more hydrophilic surface. The averaged contact angle of a contact lens, which is made of lotrafilcon A and without any coating (LbL or plasma), is about 112 degree.

EXAMPLE 3

Polyacrylic acid (PAA) solution: A solution of polyacrylic acid having a molecular weight of about 90,000, from PolyScience, is prepared by dissolving a suitable amount of the material in water to form a 0.001M PAA solution. The PAA concentration is calculated based on the repeating unit in PAA. Once dissolved, the pH of the polyanionic PAA solution is adjusted by adding 1N hydrochloric acid until the pH is about 2.5.

Poly(allylamine hydrochloride) (PAH) solution: A solution of poly(allylamine hydrochloride) (PAH) having a molecular weight of about 70,000, from Aldrich, is prepared by dissolving a suitable amount of the material in water to form a 0.001M PAH solution. The concentration is calculated based on the molecular weight of repeating unit in PAH. Thereafter, the pH of the polycationic PAH solution is measured and recorded. The pH is around 4.5

Polyvinylpyrrolidone (PVP) solution: A solution of polyvinylpyrrolidone (PVP, from Aldrich) having a molecular weight of 55,000 is prepared by dissolving a suitable amount of the material in water to form a 0.01M PVP solution. The concentration is calculated based on the repeating unit in PVP. Once dissolved, the pH of the PVP solution is adjusted by adding 1N hydrochloric acid until the pH is about 2.5.

Coating: A LbL coating having a capping layer of PVP is formed on a silicon wafer as follows. Initially, a silicon wafer is dipped in the PAH solution (0.001M, pH 2.5) for 30 minutes, optionally rinsed with a rinsing solution (water or acidified water at pH 2.5) for 1 minute, dipped in the PAA solution (0.001M, pH 2.5) for 5 minutes, optionally rinsed with the rinsing solution for 1 minute, dipped in the PAH solution for 5 minutes, and optionally rinsed with the rinsing solution for 1 minute. The silicon wafer having a coating composed three layers (PAH/PAA/PAH) is dipped in the PAA solution for 5 minutes, optionally rinsed with the rinsing solution for 1 minute, dipped in the PVP solution, optionally rinsed with the rinsing solution. By repeating the above dipping and optionally rinsing steps for a desired number of times to form a desired number of bilayers of PAA/PVP with a capping layer of PVP.

Table 1 reports the thickness of a coating on silicon wafer. The thickness of the coating on a Si wafer increases from about 9 nm (5 layers) to about 30 nm (11 layers), indicating that PAA and PVP can self-assemble into multi-layers. It is also found that the multi-bilayers of PAA/PVP can be assembled with or without water rinse steps.

TABLE 1

| Coating | Number of Layers | Thickness (nm)[1] | Thickness (nm)[2] | Thickness (nm)[3] |
| --- | --- | --- | --- | --- |
| PAH/PAA/PAH/(PAA/PVP) | 5 | 8.5 ± 0.5 | 8.0 ± 1.3 | 9.7 ± 0.6 |
| PAH/PAA/PAH/(PAA/PVP)$_2$ | 7 | 14.3 ± 0.6 | 16.8 ± 3.1 | 15.7 ± 1.4 |
| PAH/PAA/PAH/(PAA/PVP)$_3$ | 9 | 21.8 ± 1.3 | 30.5 ± 5.4 | 20.6 ± 4.6 |
| PAH/PAA/PAH/(PAA/PVP)$_4$ | 11 | 29.1 ± 2.3 | 31.1 ± 4.4 | 27.4 ± 2.9 |

[1]There is a rinsing step by dipping in water (neutral) between two dipping steps.
[2]There is a rinsing step by dipping in water (pH 2.5) between two dipping steps.
[3]There is no rinsing step between two dipping steps When a silicon wafer having an LbL coating consisting of five layers (PAH/PAA/PAH/PAA/PVP) is exposed to an acidified water (pH 2.5) for 30 minutes, there is no significant change in the thickness of the coating on a silicon wafer (i.e., the thickness changes from 8.5±0.5 to 8.6±1.5).

When a silicon wafer having an LbL coating consisting of seven layers (PAH/PAA/PAH/PAA/PVP/PAA/PVP) is subjected to an autoclave process in balanced salt solution (BSS) (pH 7.2), a patch-wise pattern can be observed on the resultant Si wafer and the thickness of the coating on a silicon wafer increases from 14.3±0.6 to 20.4±10.

When a silicon wafer having an LbL coating consisting of nine layers (PAH/PAA/PAH/PAA/PVP/PAA/PVP/PAA/PVP) is subjected to an autoclave process in water, there is no significant change in the thickness of the coating on a silicon wafer (i.e., the thickness changes from 21.8±1.3 to 19.1±2.9).

When a silicon wafer having an LbL coating consisting of eleven layers (PAH/PAA/PAH/PAA/PVP/PAA/PVP/PAA/PVP/PAA/PVP) is exposed to a phosphate buffered saline (PBS) (ca. pH 7.2), the thickness of the coating on a silicon wafer decreases from 29.1±2.3 to 3.3±0.3. However, when this silicon wafer is further subjected to an autoclave process in PBS buffer, the thickness of the coating on a silicon wafer increases from 3.3±0.3 to 51.9±10.6.

EXAMPLE 4

PAA and PVP solutions: PAA and PVP solutions are prepared as described in Example 3.

Coating: A LbL coating having a capping layer of PVP is formed on a soft contact lens made of a fluorosiloxane hydrogel material, lotrafilcon A (CIBA Vision). The contact lens is initially dipped in the PAA solution (0.001M, pH 2.5) for 30 minutes, optionally rinsed with a rinsing solution (acidified water at pH 2.5) for 1 minute, then dipped in the PVP solution (0.01M, ca. pH 2.5) for 5 minutes, and optionally rinsed with the rinsing solution for 1 minute. The above-described dipping and rinsing steps are repeated for a desired number of times to form a biocompatible LbL coating on the lens. Each of the coated lenses is placed and sealed in one glass vial filled with PBS buffer and autoclaved. After autoclave, vials containing a coated lens are not opened until lens characterization.

The coated contact lenses are not stained by Sudan black (SB), indicating that the contact lens is fully covered by the coating. As seen from table 2, PAA/PVP multi-layers were also successfully used to coat contact lenses. After only 6 dips, the coated lenses have contact angles of about 75 to 85 degrees and COF of about 3.4 (as compared to about a COF of ~4 for un-coated lenses).

TABLE 2

| Coating | Contact angle[a] | | COF | SB staining |
| --- | --- | --- | --- | --- |
| Uncoated contact lens (Control) | 110 | | ~4.0 | stain |
| PAA/PVP/PAA/PVP/PAA/PVP[d] | 75 ± 10[b] | 76 ± 10[c] | 3.46 ± 0.28 | clear |
| PAA/PVP/PAA/PVP/PAA/PVP[e] | 80 ± 3[b] | 85 ± 10[c] | 3.44 ± 0.14 | clear |

[a]A value obtained by averaging the measurements of three contact lenses.
[b]Determined before autoclave.
[c]Determined after autoclave.
[d]There is a rinsing step (dipping in water at pH 2.5 for 1 minute) between two dipping steps.
[e]There is no rinsing step between two dipping steps.

EXAMPLE 5

PAA and PVP solutions: PAA and PVP solution are prepared as described in Example 3.

PAAm-co-PAA solution: A solution of PAAm-co-PAA copolymer (80% PAAm ad 20% PAA, from Advanced Research Unit, Ciba Vision Switzerland) is prepared by dissolving a suitable amount of the material in water to form a 0.0001M solution. The PAAm-co-PAA copolymer concentration is calculated based on the molecular weight of repeat unit. Once dissolved, the pH of the PAAm-co-PAA solution is adjusted to pH 2.5 by adding 1N hydrochloric acid.

Coating A: A coating having multiple bilayers of PVP/PAAm-co-PAA is formed on a silicon wafer or a soft contact lens made of a fluorosiloxane hydrogel material, lotrafilcon A (CIBA Vision). The contact lens (or silicon wafer) is dipped in the PAA solution (0.001M, pH 2.5) for 30 minutes to form a first layer on the lens. The lens (or silicon wafer) with a first layer of PAA is then dipped in the PVP solution (0.0001M, pH 2.5) for 5 minutes and then dipped in the PAAm-co-PAA solution for 5 minutes. Finally, the steps of dipping in the PVP solution for 5 minutes followed by dipping in the PAAm-co-PAA solution for 5 minutes are repeated for a desired number of times to build up a desired number of bilayers of PVP/PAAm-co-PAA on the lens (or silicon wafer). There is no rinsing step involved in the above coating process. Each of the coated lenses is placed and sealed in one glass vial filled with PBS buffer and autoclaved. After autoclave, vials containing a coated lens are not opened until lens characterization.

Silicon wafers and contact lenses with LbL coatings, which comprises two or more bilayers of PVP/PAAm-co-PAA are characterized and results are reported in Table 3.

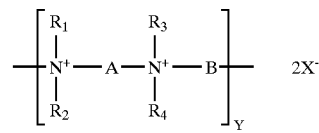

in which $R_1$, $R_2$, $R_3$, and $R_4$ are methyl radicals, and A and B are hexamethylene and decamethylene groups respectively, is prepared by dissolving a suitable amount of PQ6-10 in water to have a concentration of 300 ppm. Once dissolved, the pH of the PQ6-10 solution is adjusted to pH 5.6.

Coating A: A coating having the innermost layer of PAA, 4 bilayers of PVP/PVP-co-PAA and one capping bilayer of PVP/PAA (i.e., PAA/PVP/PVP-co-PAA/PVP/PVP-co-PAA/PVP/PVP-co-PAA/PVP/PVP-co-PAA/PVP/PAA) is formed on a silicon wafer or a soft contact lens made of a fluorosiloxane hydrogel material, lotrafilcon A (CIBA Vision). The contact lens (or silicon wafer) is dipped in the PAA solution (0.001M, pH 2.5) for 30 minutes to form the innermost layer of the coating on the lens. The lens (or silicon wafer) with the innermost layer of PAA is then dipped in the PVP solution (0.0001M, pH 2.5) for 5 minutes and then dipped in the PVP-co-PAA solution for 5 minutes. The steps of dipping in the PVP solution for 5 minutes followed by dipping

TABLE 3

| Coating | Thickness (nm)[a] | Contact angle[b] |
|---|---|---|
| PAA/PVP/PAAm-co-PAA/PVP/PAAm-co-PAA | 6.0 ± 1.2 | 58 ± 10 |
| PAA/PVP/PAAm-co-PAA/PVP/PAAm-co-PAA/PVP/PAAm-co-PAA/PVP/PAAm-co-PAA | 8.7 ± 2.1 | 29 ± 2 |

[a]Determined on Si wafers.
[b]determined on lenses.

The experimental results confirm that an LbL coating comprising multi-bilayer of PVP/PAAm-co-PAA can be successfully applied onto a silicon wafer or a contact lens. The coated lenses have a contact angles of about 58 degrees when having one layer of PAA and 2 bilayers of PVP/PAAm-co-PAA and have a contact angles of about 30 degrees when having one layer of PAA and 4 bilayers of PVP/PAAm-co-PAA. The uncoated contact lenses have a contact angles of about 110 degrees.

EXAMPLE 6

PAA solution: A PAA solution is prepared as described in Example 3.

PVP solution: A PVP solution is prepared according to a procedure similar to that described in Example 3. The concentration of PVP is 0.001M (pH 2.5).

PVP-co-PAA solution: A solution of PVP-co-PAA copolymer (75% PVP ad 25% PAA, from Aldrich, is prepared by dissolving a suitable amount of the material in water to form a 0.001M solution. The PVP-co-PAA copolymer concentration is calculated based on the molecular weight of repeat unit. Once dissolved, the pH of the PVP-co-PAA solution is adjusted to pH 2.5.

PQ6-10 solution: A solution of polyquat (PQ6-10) of the following formula in the PVP-co-PAA solution for 5 minutes are repeated for 4 times to build up 4 bilayers of PVP/PVP-co-PAA on the lens (or silicon wafer). The lens (or silicon wafer) with the innermost layer of PAA and 4 bilayers of PVP/PVP-co-PAA is dipped in the PVP solution for 5 minute and then dipped in the PAA solution. There is no rinsing step involved in the above coating process. Each of the coated lenses is placed and sealed in one glass vial filled with PBS buffer and autoclaved. After autoclave, vials containing a coated lens are not opened until lens characterization.

Coating B: A coating having the innermost layer of PAA, 4 bilayers of PVP/PVP-co-PAA, one bilayer of PVP/PAA and a capping layer of PQ6-10 (i.e., PA/PVP/PVP-co-PAA/PVP/PVP-co-PAA/PVP/PVP-co-PAA/PVP/PVP-co-PAA/PVP/PAA/PQ6-10) is formed on a silicon wafer or a soft contact lens made of a fluorosiloxane hydrogel material, lotrafilcon A (CIBA Vision). The contact lens (or silicon wafer) is dipped in the PAA solution (0.001M, pH 2.5) for 30 minutes to form the innermost layer of the coating on the lens. The lens (or silicon wafer) with the innermost layer of PAA is then dipped in the PVP solution (0.0001M, pH 2.5) for 5 minutes and then dipped in the PVP-co-PAA solution for 5 minutes. The steps of dipping in the PVP solution for 5 minutes followed by dipping in the PVP-co-PAA solution for 5 minutes are repeated for 4 times to build up 4 bilayers of PVP/PVP-co-PAA on the lens (or silicon wafer). The lens (or silicon wafer) with the innermost layer of PAA and 4 bilayers of PVP/PVP-co-PAA is dipped in the PVP solution for 5 minute, then dipped in the PAA solution, and finally dipped in the PQ6-10 solution. There is no rinsing step involved in the above coating process. Each of the coated lenses is placed and sealed in one glass vial filled with PBS buffer and autoclaved. After autoclave, vials containing a coated lens are not opened until lens characterization.

Silicon wafers and contact lenses with LbL coatings are characterized and results are reported in Table 4.

TABLE 4

| Coating | Thickness (nm)[a] | Contact angle[b] |
|---|---|---|
| A (PAA/PVP/PVP-co-PAA/PVP/PVP-co-PAA/PVP/PVP-co PAA/PVP/PVP-co-PAA/PVP/PAA) | 7 | 36 ± 3 |
| B (PAA/PVP/PVP-co-PAA/PVP/PVP-co-PAA/PVP/PVP-co PAA/PVP/PVP-co-PAA/PVP/PAA/PQ6-10) | 17 | 25 ± 4 |

[a]Determined on Si wafers.
[b]Determined on lenses.

The experimental results confirm that an LbL coating (coating A or coating B) can be successfully applied onto a silicon wafer or a contact lens. The coated lenses have a substantially increased hydrophilicity characterized by a contact angles of about 36 degrees for coating A and a contact angles of about 25 degrees for coating B. The uncoated contact lenses have a contact angles of about 110 degrees.

EXAMPLE 7

PAA solutions: Three PAA solutions (pH 2.5) respectively containing 0.0001 M, 0.001 M and 0.01 M PAA are prepared as described in Example 3.

PVP solution: A PVP solution is prepared according to a procedure similar to that described in Example 3.

Coating: A LbL coating having a multi-bilayer of PAA/PVP is formed on a soft contact lens made of a fluorosiloxane hydrogel material, lotrafilcon A (CIBA Vision). The contact lens is initially dipped in a first PAA solution (0.0001 M, 0.001 M or 0.01 M, pH 2.5) for 30 minutes to form the innermost layer of the coating. The lens with the innermost layer of PAA is dipped in the PVP solution (0.0001M, about pH 2.5) for 5 minutes and then dipped in a PAA solution (0.0001 M, pH 2.5). The steps of dipping in the PVP solution (0.0001 M, about pH 2.5) and dipping in the PAA solution (0.0001M, about pH 2.5) are repeated for 4 times. A capping layer of PVP is applied to the coated lens by dipping in the PAA solution (0.0001M, about pH 2.5). Each of the coated lenses is placed and sealed in one glass vial filled with PBS buffer and autoclaved. After autoclave, vials containing a coated lens are not opened until lens characterization.

It is found that the PAA concentration used in the formation of the innermost layer has significant effect on the hydrophilicity of coated contact lenses. The contact angle obtained by averaging measurements of 10 contact lenses (before autoclave) decreases from 59±8 degrees, to 43±7 degrees and to 38±9 degrees, when the concentration of PAA increases from 0.0001 M, to 0.001 M, to 0.01 M. Similarly, the contact angle obtained by averaging measurements of 10 contact lenses (after autoclave) decreases from 65±7 degrees, to 54±5 degrees and to 52±7 degrees, when the concentration of PAA increases from 0.0001M, to 0.001M, to 0.010 M. The uncoated contact lenses have a contact angle of about 110 degrees.

EXAMPLE 8

PAA, PAH and PVP solutions: PAA, PAH, PVP solutions are prepared as described in Example 3.

An LbL coating procedure is tried to build up multi-bilayers of PAH/PVP on a silicon wafer. The silicon wafer is dipped in the PAH solution (0.0001 M, pH 2.5) for 30 minutes, optionally rinsed with a rinsing solution (acidified water pH 2.5) for 1 minute, dipped in the PVP solution (0.0001M, approx. pH 2.5) for 5 minutes, and the optionally rinsed with the rinsing solution for 1 minute. By repeating the 5-minute dip coating steps first in the PAH solution and then in the PVP solution and optionally 1 minute-rinsing step between two dip-coating step for a number of times (3, 5, 7, 9 times). After the LbL coating process is completed, the thickness of coating on the silicon wafer is determined and results are reported in Table 5. Table 5 shows that the thickness of a coating on the silicon wafer does not increase as the number of iterative dip-coatings increases, indicating that multi-bilayers of PAH/PVP may not be efficiently built-up on a silicon wafer under the coating conditions in the study.

TABLE 5

| Successive Coating Solutions | Coating Thickness (nm)[a] |
|---|---|
| PAH, PVP, PAH, PVP, PAH, PVP, PAH, PVP | 2.7 ± 0.4 |
| PAH/PVP, PAH, PVP, PAH, PVP, PAH, PVP, PAH, PVP, PAH, PVP | 2.4 ± 0.2 |
| PAH/PVP, PAH, PVP, PAH, PVP, PAH, PVP, PAH, PVP, PAH, PVP, PAH, PVP, PAH, PVP | 3.2 ± 0.6 |
| PAH/PVP, PAH, PVP, PAH, PVP, PAH, PVP, PAH, PVP, PAH, PVP, PAH, PVP, PAH, PVP, PAH, PVP | 3.2 ± 0.5 |

[a]Averaged coating thickness on a silicon wafer is determined by averaging the measurements of 4 silicon wafers.

Although various embodiments of the invention have been described using specific terms, devices, and methods, such description is for illustrative purposes only. The words used are words of description rather than of limitation. It is to be understood that changes and variations may be made by those skilled in the art without departing from the spirit or scope of the present invention, which is set forth in the following claims. In addition, it should be understood that aspects of the various embodiments may be interchanged either in whole or in part. Therefore, the spirit and scope of the appended claims should not be limited to the description of the preferred versions contained therein.

What is claimed is:

1. A medical device, comprising a core material and a biocompatible LbL coating non-covalently attached to said core material, wherein said biocompatible LbL coating comprises at least one charge/non-charge bilayer, wherein said charge/non-charge bilayer is composed of, in no particular order, one layer of a charged polymeric material and one layer of a non-charged polymeric material which is capable of being non-covalently bond to the charged polymeric material, wherein said charged polymeric material is a first polyanionic polymer or a mixture of two or more polyanionic polymers, and wherein said non-charged material is a homopolymer of a vinyl lactam of formula (I), a coplymer of at least one vinyl lactam of formula (I) in the presence or in the absence of one or more hydrophilic vinylic comonomers, or mixture thereof

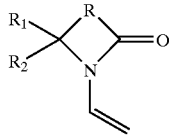

(I)

wherein
R is an alkylene di-radical having from 2 to 8 carbon atoms,
$R_1$ is hydrogen, $C_1$–$C_{10}$ alkyl, aryl having up to 10 carbon atoms, aralkyl or alkaryl having up to 14 carbon atoms, and
$R_2$ is hydrogen or $C_1$–$C_{10}$ alkyl.

2. A medical device of claim 1, wherein said medical device is an ophthalmic device.

3. A medical device of claim 2, wherein said ophthalmic device is a contact lens.

4. A contact lens of claim 3, wherein said core material is a hydrogel.

5. A contact lens of claim 4, wherein said hydrogel is a siloxane-containing polymer.

6. A medical device of claim 2, wherein R is a $C_2$–$C_4$ alkylene di-radical, and wherein $R_1$ and $R_2$ are each independently of the other hydrogen or $C_1$–$C_7$ alkyl.

7. A medical device of claim 2, wherein said non-charged material is a homopolymer of N-vinyl-2-pyrrolidone, N-vinyl-2-piperidone, N-vinyl-2-caprolactam, N-vinyl-3-methyl-2-pyrrolidone, N-vinyl-3-methyl-2-piperidone, N-vinyl-3-methyl-2-caprolactam, N-vinyl-4-methyl-2-pyrrolidone, N-vinyl4-methyl-2-caprolactam, N-vinyl-5-methyl-2-pyrrolidone, N-vinyl-5-methyl-2-piperidone, N-vinyl-5,5-dimethyl-2-pyrrolidone, N-vinyl-3,3,5-trimethyl-2-pyrrolidone, N-vinyl-5-methyl-5-ethyl-2-pyrrolidone, N-vinyl-3,4,5-trimethyl-3-ethyl-2-pyrrolidone, N-vinyl-6-methyl-2-piperidone, N-vinyl-6-ethyl-2-piperidone, N-vinyl-3,5-dimethyl-2-piperidone, N-vinyl-4,4-dimethyl-2-piperidone, N-vinyl-7-methyl-2-caprolactam, N-vinyl-7-ethyl-2-caprolactam, N-vinyl-3,5-dimethyl-2-caprolactam, N-vinyl-4,6-dimethyl-2-caprolactam or N-vinyl-3,5,7-trimethyl-2-caprolactam.

8. A medical device of claim 7, wherein said non-charged material is a copolymer of two or more of N-vinyl-2-pyrrolidone, N-vinyl-2-piperidone, N-vinyl-2-caprolactam, N-vinyl-3-methyl-2-pyrrolidone, N-vinyl-3-methyl-2-piperidone, N-vinyl-3-methyl-2-caprolactam, N-vinyl-4-methyl-2-pyrrolidone, N-vinyl-4-methyl-2-caprolactam, N-vinyl-5-methyl-2-pyrrolidone, N-vinyl-5-methyl-2-piperidone, N-vinyl-5,5-dimethyl-2-pyrrolidone, N-vinyl-3,3,5-trimethyl-2-N-vinyl-5-methyl-5-ethyl-2-pyrrolidone, N-vinyl-3,4,5-trimethyl-3-ethyl-2-pyrrolidone, N-vinyl-6-methyl-2-piperidone, N-vinyl-6-ethyl-2-piperidone, N-vinyl-3,5-dimethyl-2-piperidone, N-vinyl-4,4-dimethyl-2-piperidone, N-vinyl-7-methyl-2-caprolactam, N-vinyl-7-ethyl-2-caprolactam, N-vinyl-3,5-dimethyl-2-caprolactam, N-vinyl-4,6-dimethyl-2-caprolactam and N-vinyl-3,5,7-trimethyl-2-caprolactam.

9. A medical device of claim 2, wherein said first polyanionic polymer is a copolymerization product of acrylic acid, methacrylic acid, or mixture thereof with acrylamide, N,N-dimethyl acrylamide, N-vinyl-2-pyrrolidone, N-vinyl-2-piperidone, N-vinyl-2-caprolactam, N-vinyl-3-methyl-2-pyrrolidone, N-vinyl-3-methyl-2-piperidone, N-vinyl-3-methyl-2-caprolactam, N-vinyl-4-methyl-2-pyrrolidone, N-vinyl-4-methyl-2-caprolactam, N-vinyl-5-methyl-2-pyrrolidone, N-vinyl-5-methyl-2-piperidone, N-vinyl-5,5-dimethyl-2-pyrrolidone, N-vinyl-3,3,5-trimethyl-2-pyrrolidone, N-vinyl-5-methyl-5-ethyl-2-pyrrolidone, N-vinyl-3,4,5-trimethyl-3-ethyl-2-pyrrolidone, N-vinyl-6-methyl-2-piperidone, N-vinyl-6-ethyl-2-piperidone, N-vinyl-3,5-dimethyl-2-piperidone, N-vinyl-4,4-dimethyl-2-piperidone, N-vinyl-7-methyl-2-caprolactam, N-vinyl-7-ethyl-2-caprolactam, N-vinyl-3,5-dimethyl-2-caprolactam, N-vinyl-4,6-dimethyl-2-caprolactam, N-vinyl-3,5,7-trimethyl-2-caprolactam, or mixtures thereof.

10. A medical device of claim 2, wherein said biocompatible LbL coating further comprises at least one layer of a polycationic polymer or of a mixtures of polycationic polymers.

11. A medical device of claim 2, wherein said biocompatible LbL coating comprises 2 to 20 charge/non-charge bilayers.

12. A medical device of claim 11, wherein said biocompatible LbL coating comprises 4 to 10 charge/non-charge bilayers.

13. A medical device of claim 2, wherein said biocompatible LbL coating further comprises at least one layer of second polyanionic polymer.

* * * * *